US00PP11462P

United States Patent [19]

Willmeng

[11] Patent Number: Plant 11,462

[45] Date of Patent: Jul. 25, 2000

[54] PEACH TREE NAMED 'WB 258'

[75] Inventor: Randy Willmeng, Watervliet, Mich.

[73] Assignee: Hilltop Nurseries LLC, Hartford, Mich.

[21] Appl. No.: 09/084,553

[22] Filed: May 26, 1998

[51] Int. Cl.[7] ..... A01H 5/00

[52] U.S. Cl. ..... Plt./197

[58] Field of Search ..... Plt./197

[56] References Cited

U.S. PATENT DOCUMENTS

P.P. 3,179 5/1972 Paul ..... Plt./197

P.P. 9,129 5/1995 Friday ..... Plt./197

*Primary Examiner*—Howard J. Locker

*Assistant Examiner*—Wendy Baker

*Attorney, Agent, or Firm*—Flynn, Thiel, Boutell & Tanis, P.C.

[57] ABSTRACT

A new and distinct variety of peach tree, which has been given the designation 'WB 258', that is cold hardy, disease resistant, productive and bears an attractively colored fruit of good size and quality that is suitable for long distance shipping.

4 Drawing Sheets

FIELD OF THE INVENTION

The present invention relates to a peach tree variety and more specifically to a peach tree variety that is cold hardy and disease resistant bearing a high-quality, early season peach for the fresh market.

BACKGROUND OF THE INVENTION

'WB 258' peach (*Prunus persica* L. Batsch) is a fresh market peach which is distinguished in characteristics from the varieties similar to it. 'Garnet Beauty' is the variety it most closely resembles.

'WB 258' peach is an early season peach that ripens six days before 'Red Haven', is cold hardy, disease resistant, productive, bears very attractively colored fruit of good size and quality, and is suitable for long-distance shipping. 'WB 258' should be adapted to temperate and other regions where 'Garnet Beauty' is successfully grown. To Applicant's knowledge, none of the prior art varieties referred to herein are patented.

SUMMARY OF THE INVENTION

The new and distinct peach tree variety, which has been given the designation of 'WB 258', produces a high quality early season peach. Its fruit ripens just before 'Garnet Beauty'.

DETAILED DESCRIPTION OF THE INVENTION

Figure 1:
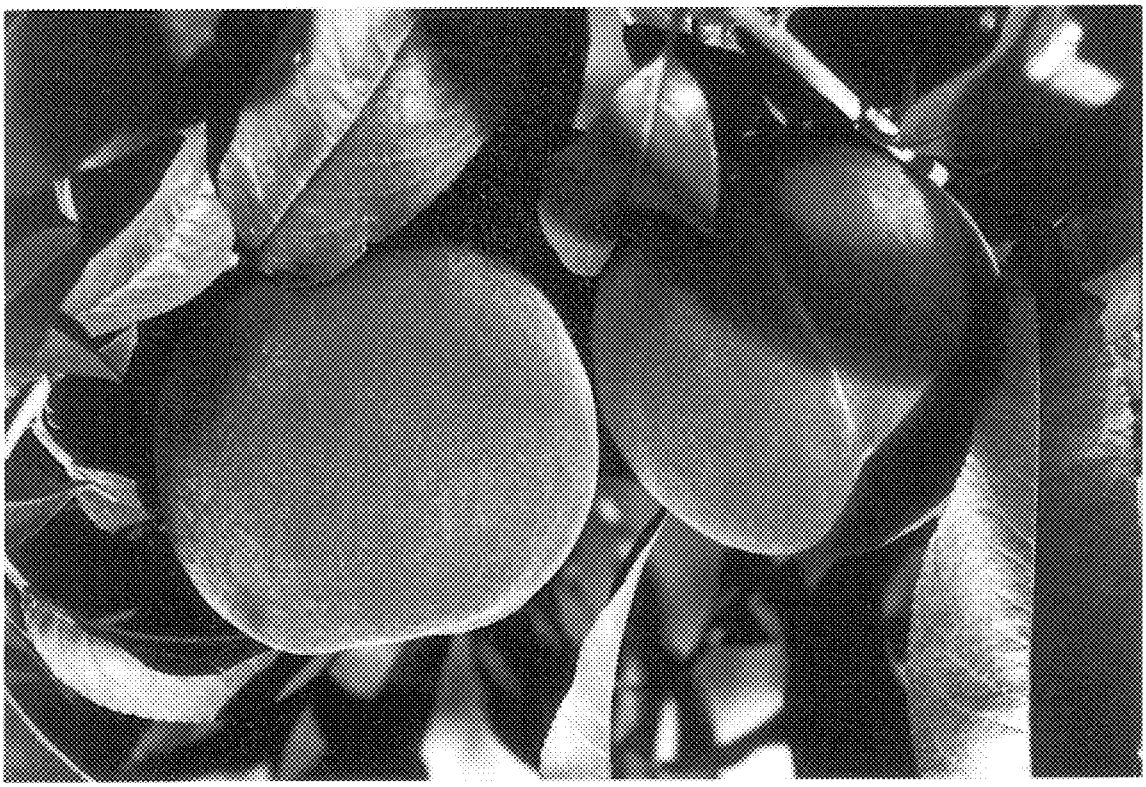
FIG. 1 is a photographic illustration of the whole fruit of the variety with accompanying foliage.
Figure 2:
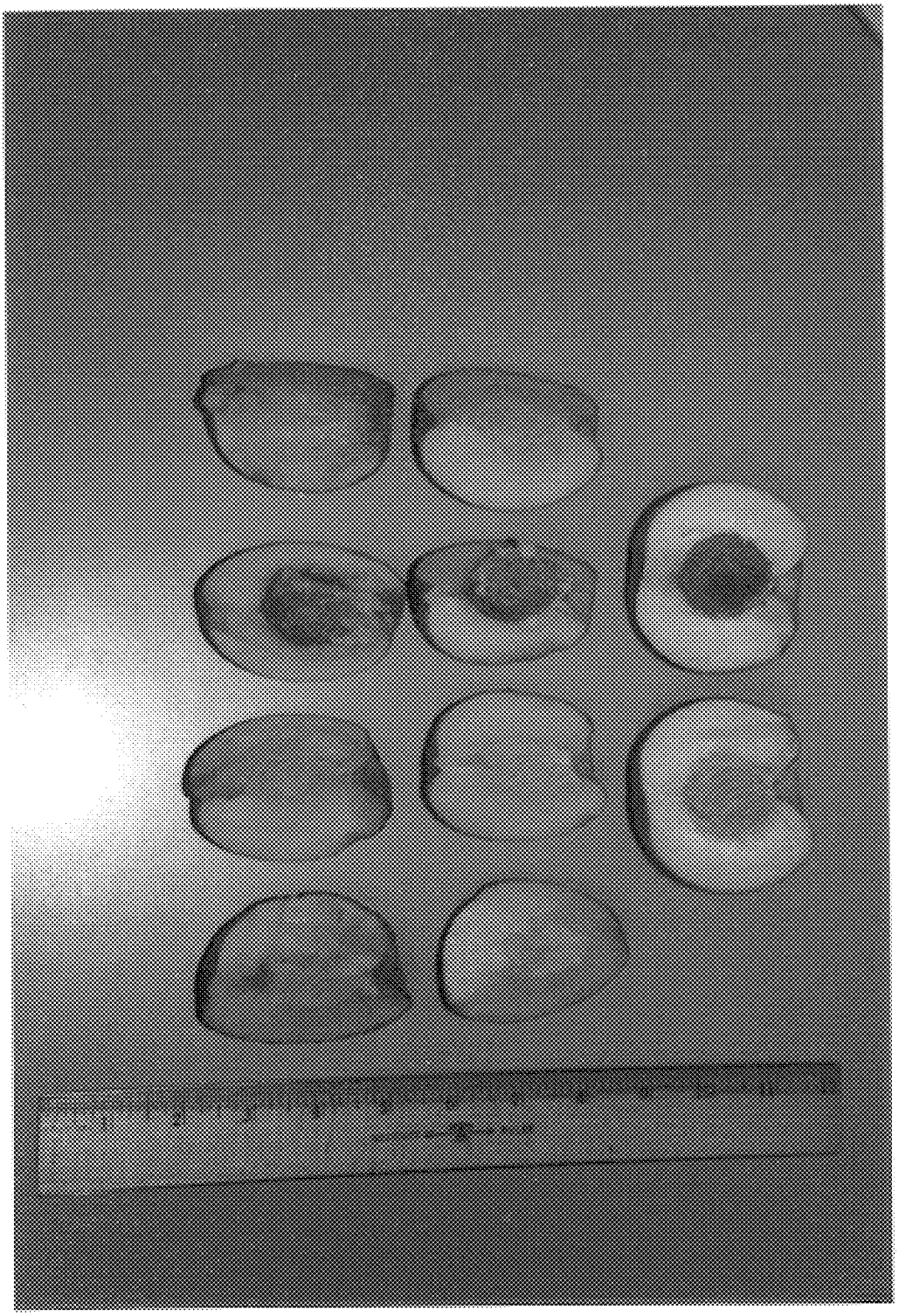
FIG. 2 is a photographic illustration of three specimen of the fruit of the variety that have been sectioned. It shows sections with the stone removed to expose the pit well as well as sections with the stone left in place.
Figure 3:
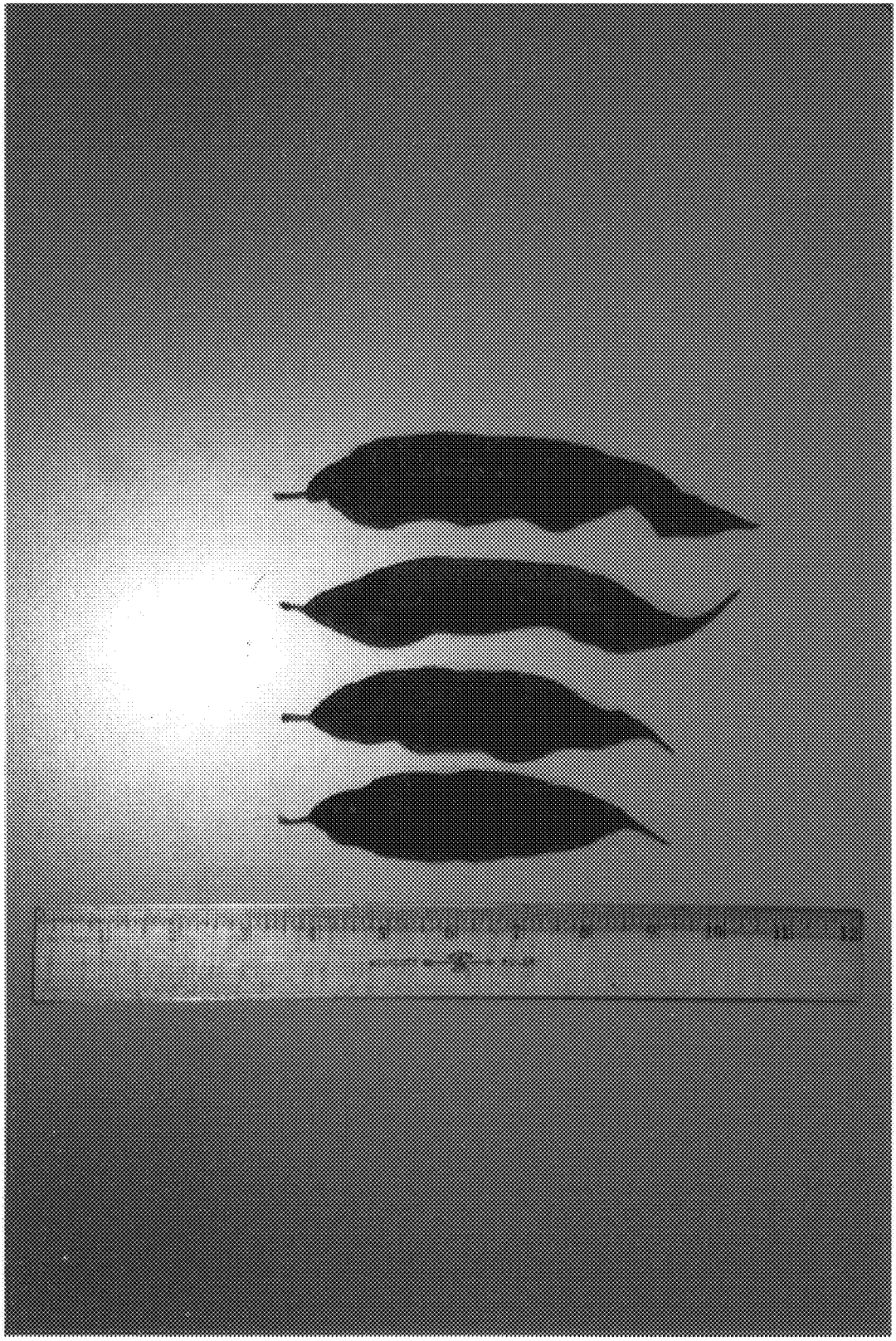
FIG. 3 is a photographic illustration of the leaves and petioles of the variety.
Figure 4:
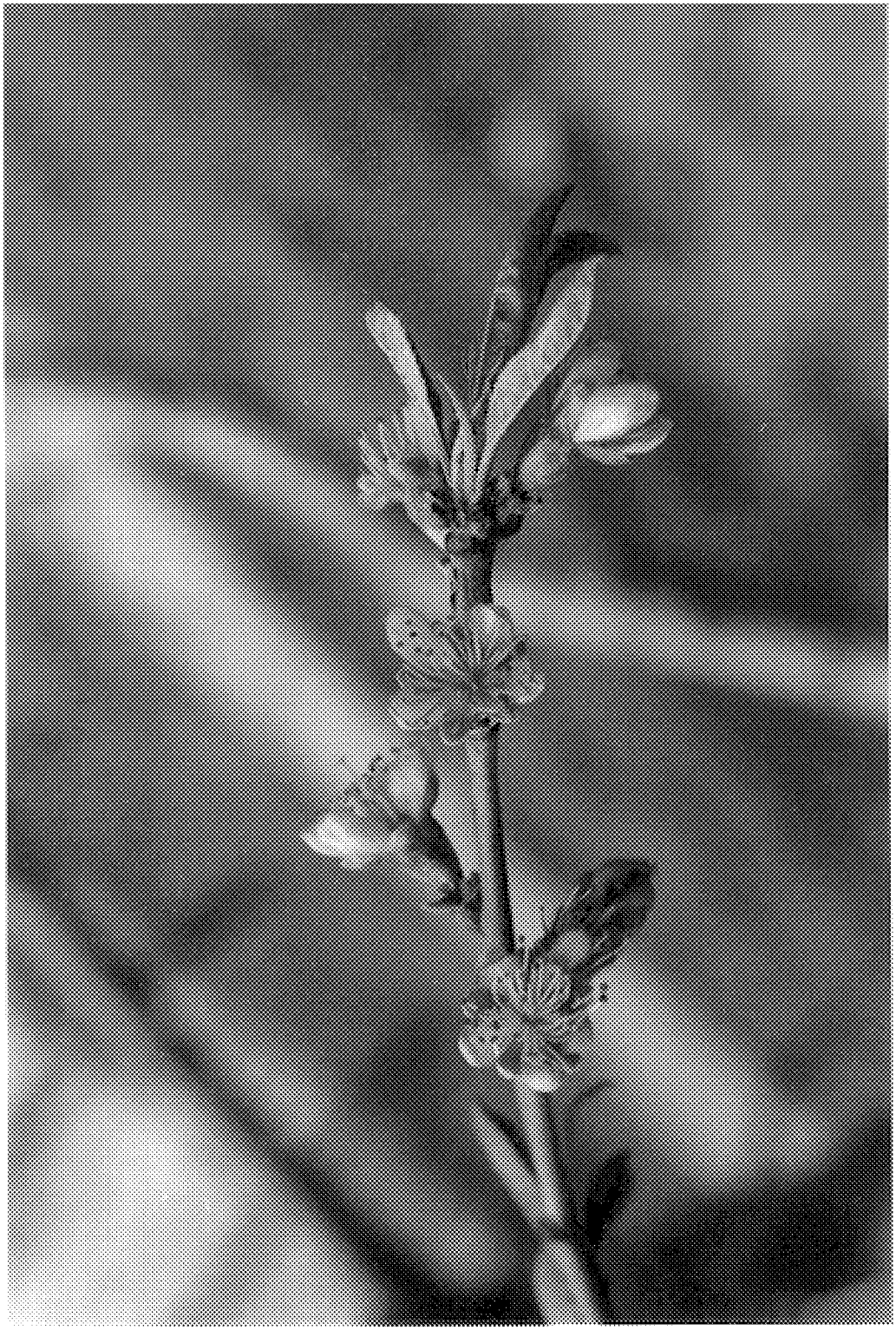
FIG. 4 is a photographic illustration of the flowers and buds of the variety.

'WB 258' originated as a limb mutation of 'Garnet Beauty' in Watervliet, Mich. After selection, 'WB 258' was then propagated by budding on peach seedling rootstocks in the same location and tested. 'WB 258' remains stable through succeeding asexual propagation and it is self-pollinated.

The tree habit of 'WB 258' is medium, vigorous, open and spreading. The tree has a normal annual growth of 24 to 30 inches and it reaches an average tree height of 9 feet at thee years. 'WB 258' is vase formed, is medium productive to productive and regular bearing. The leaves are medium size and abruptly pointed compared with the medium to large size of 'Garnet Beauty'. The shape of the fruit tip is dimpled and the symmetry along the suture is symmetric in contrast to 'Garnet Beauty' which is asymmetric.

The size of the stone is medium to small and its shape is ovid. The percentage of split or shattered stones is very low as compared to 'Garnet Beauty'. The stone adheres to the flesh.

The fruits of 'WB 258' have an average 1 week picking season. The prominence of the suture is distinct for 'WB 258' and high for 'Garnet Beauty'. Anthocyanin coloration of the skin is brighter red for 'WB 258' than for 'Garnet Beauty'. More fruit surface of 'WB 258' is covered with a red blush compared with 'Garnet Beauty'. There is no anthocyanin coloration around the stone unlike 'Garnet Beauty' where it is present. Pubescence on skin is short and sparse. The flesh adheres more to the stone for 'WB 258' than for 'Garnet Beauty'.

The color terminology is in accordance with The Ridgeway Color Standards.

Tree:

*Size.*—Medium.

*Vigor.*—Vigorous.

*Habit.*—Open, Spreading. Vase Formed. Hardy.

*Productivity.*—Average on mature trees 350–400 bushels per acre. Regular Bearer.

Trunk:

*Size.*—Medium. Medium Smoothness.

Branches: Medium. Medium smoothness. Gray. Glossy.
Lenticels: Medium. Large.
Leaves:
*Length.*—5½" to 6½" (excluding the petioles).
*Width.*—1¼" to 1½".
*Size.*—Medium. Abruptly pointed.
*Color.*—Upper surface Medium Green–Forest Green (Plate XVII 29'm). Lower surface — slightly lighter green.
Margin: Crenate (or serrulate).
Petiole:
*Length.*—⅜" to ½".
*Thickness.*—1/16" to ⅛".
Glands: Average Number: 2. Opposite. Some large, some small. Reniform.
Flowers:
*Dates first and full blossom.*—April 10–15. Medium blossoming compared with other varieties.
*Size.*—Small.
*Color.*—Rose pink (XII 71f), non-showy.
Fruit: Maturity when described —
*Eating.*—Date Jul. 17, 1995.
Size: Uniform. Axial Diameter 2⅝". Transverse in suture plane 2½". At right angles to suture plane 2⅝".
Shape: Uniform, symmetrical, Oblate to Globose.
Suture: Distinct, prominent; sometimes yellow, Extends from base to beyond but discontinues at apex over entire circumference; has slight marked depression beyond pistil point.
Ventral surface: Rounded; No lips.
Cavity: Rounded; Elongated in suture.
*Depth.*—¼".
*Breadth.*—¾".
Base: Truncate — rounded.
Apex: Short.
Stem: Length 1/16", stout, Pubescent Medium adherence to stone.

Skin:
*Thickness.*—Medium; Tender; Adheres strongly to flesh.
*Color.*—Highly blushed red; 75–85% dark mottled red; mostly Brazil Red 1-5i to Peach Red 1-5R Ground color when ripe is yellow.
Flesh:
*Color.*—Buff Yellow (IV 19d), mottled with red under skin, little red around pit. Surface of pit cavity — Buff Yellow (IV 19d).
*Amygdalin.*—Scant.
*Texture.*—Melting.
*Fibers.*—Few, coarse.
*Ripens.*—Fairly even.
*Flavor.*—Good flavor subacid, with balance between sweetness and acidity.
*Aroma.*—Pronounced.
*Eating quality.*—Good.
Stone:
*Size.*—Medium to Small.
*Free.*—Cling.
*Form.*—Ovid at apex.
*Base.*—Oval.
*Sides.*—Unequal.
*Surface.*—Regularly; furrowed near base; pitted toward base throughout.
*Length.*—1".
*Width.*—⅝".
Keeping quality: Medium; Stores up to 3 weeks at 35° F.
Resistance to insects: Good against most Michigan insect pests.
Resistance to diseases: Medium resistance to Bacterial Spot and Peach Canker.
Shipping quality: Medium.

I claim:

1. A new and distinct peach tree variety substantially as shown and described herein.

* * * * *